United States Patent
Barak et al.

(10) Patent No.: US 7,063,676 B2
(45) Date of Patent: Jun. 20, 2006

(54) AUTOMATIC PORTABLE PNEUMATIC COMPRESSION SYSTEM

(75) Inventors: Jakob Barak, Oranit (IL); Yoav Naveh, Atlit (IL); Sharon Ehrlich, Beit-Herot (IL)

(73) Assignee: Medical Compression Systems (DBN) Ltd., Or-Aqiva (IL)

( * ) Notice: Subject to any disclaimer, the term of this patent is extended or adjusted under 35 U.S.C. 154(b) by 505 days.

(21) Appl. No.: 09/941,909

(22) Filed: Aug. 29, 2001

(65) Prior Publication Data

US 2002/0042583 A1    Apr. 11, 2002

Related U.S. Application Data

(63) Continuation of application No. 09/413,968, filed on Oct. 7, 1999, now Pat. No. 6,494,852, which is a continuation-in-part of application No. 09/038,157, filed on Mar. 11, 1998, now Pat. No. 6,478,757.

(51) Int. Cl.
*A61H 9/00* (2006.01)
*A61H 23/04* (2006.01)

(52) U.S. Cl. .................. 601/150; 601/149; 601/152; 602/13

(58) Field of Classification Search ........ 601/148–152; 602/13; 606/201, 202
See application file for complete search history.

(56) References Cited

U.S. PATENT DOCUMENTS

| | | | |
|---|---|---|---|
| 2,823,668 A * | 2/1958 | Court et al. ........... 602/13 |
| 2,880,721 A | 4/1959 | Corcoran | |
| 2,896,612 A * | 7/1959 | Bates et al. ........... 601/149 |
| 3,164,152 A * | 1/1965 | Vere ................... 602/13 |
| 3,186,405 A * | 6/1965 | Bailey et al. .......... 602/13 |
| 3,424,151 A * | 1/1969 | Ericson ................ 602/13 |
| 3,454,010 A | 7/1969 | Lilligren et al. | |
| 3,548,809 A | 12/1970 | Conti | |
| 3,811,431 A * | 5/1974 | Apstein ................ 601/150 |
| 3,892,229 A * | 7/1975 | Taylor et al. .......... 601/152 |
| 4,029,087 A * | 6/1977 | Dye et al. ............. 601/152 |
| 4,157,713 A * | 6/1979 | Clarey ................. 602/13 |
| 4,206,751 A * | 6/1980 | Schneider ............. 601/152 |
| 4,266,298 A * | 5/1981 | Graziano .............. 2/22 |
| 4,402,312 A | 9/1983 | Villari et al. | |
| 4,418,690 A * | 12/1983 | Mummert .............. 601/152 |
| 4,573,453 A | 3/1986 | Tissot | |
| 4,597,384 A * | 7/1986 | Whitney ............... 601/152 |
| 4,682,587 A * | 7/1987 | Curlee ................ 602/13 |
| 4,682,588 A * | 7/1987 | Curlee ................ 602/13 |
| 4,773,397 A * | 9/1988 | Wright et al. ......... 601/151 |
| 4,858,596 A | 8/1989 | Kolstedt et al. | |
| 5,007,411 A | 4/1991 | Dye | |
| 5,014,681 A * | 5/1991 | Heeman et al. ........ 601/152 |

(Continued)

FOREIGN PATENT DOCUMENTS

DE    19 03 217    4/1970

(Continued)

*Primary Examiner*—Stephen K. Cronin
*Assistant Examiner*—Victor K. Hwang
(74) *Attorney, Agent, or Firm*—Gauthier & Connors LLP

(57) ABSTRACT

An automatic portable ambulant miniaturized system for applying pneumatic pressure to a body limb including a portable ambulant hand-held fluid source unit, a conduit for delivering fluid generated by the unit, and a sleeve coupled to the conduit and adapted to envelop a body limb. The sleeve contains one or more individually inflatable cells, each cell being subdivided into two or more longitudinally extending confluent compartments along the axis of the body limb. The compartments are inflated and deflated essentially simultaneously by the portable fluid source unit.

45 Claims, 13 Drawing Sheets

U.S. PATENT DOCUMENTS

| | | | |
|---|---|---|---|
| 5,025,781 A | 6/1991 | Ferrari | |
| 5,109,832 A * | 5/1992 | Proctor et al. | 601/149 |
| 5,117,812 A | 6/1992 | McWhorter | |
| 5,179,941 A * | 1/1993 | Siemssen et al. | 601/152 |
| 5,186,163 A * | 2/1993 | Dye | 601/27 |
| 5,211,162 A | 5/1993 | Gillen, Jr. et al. | |
| 5,218,954 A | 6/1993 | van Bemmelen | |
| 5,288,286 A | 2/1994 | Davis | |
| 5,368,547 A | 11/1994 | Polando | |
| 5,575,762 A * | 11/1996 | Peeler et al. | 601/152 |
| 5,588,955 A | 12/1996 | Johnson, Jr. et al. | |
| 5,591,200 A | 1/1997 | Cone et al. | |
| 5,634,889 A | 6/1997 | Gardner et al. | |
| 5,713,954 A * | 2/1998 | Rosenberg et al. | 600/17 |
| 5,728,055 A * | 3/1998 | Sebastian | 602/19 |
| 5,795,312 A * | 8/1998 | Dye | 601/151 |
| 5,800,528 A | 9/1998 | Lederman et al. | |
| 5,810,750 A * | 9/1998 | Buser | 602/13 |
| 5,843,007 A | 12/1998 | McEwen et al. | |
| 6,007,559 A * | 12/1999 | Arkans | 606/201 |
| 6,254,556 B1 * | 7/2001 | Hansen et al. | 601/149 |
| 6,315,745 B1 * | 11/2001 | Kloecker | 602/13 |

FOREIGN PATENT DOCUMENTS

| | | | |
|---|---|---|---|
| DE | 27 10 677 | 9/1978 | |
| EP | 388 200 | 9/1990 | |
| FR | 2 122 734 | 9/1972 | |
| GB | 2 017 508 | 10/1979 | |
| JP | 8-38562 * | 2/1996 | |
| JP | 9-182771 * | 7/1997 | |
| SU | 1452523 | 1/1989 | 601/152 |
| TW | 137881 | 9/1988 | |

* cited by examiner

|  | T1 | T2 | T3 | T4 | T5 | T6 | T7 |
|---|---|---|---|---|---|---|---|
| Valve 1 | + | - | - | - | - | - | - |
| Valve 2 | + | + | - | + | + | + | + |
| Valve 3 | + | + | + | + | + | + | + |
| Valve 4 | + | + | + | + | + | + | - |
| Valve 5 | - | - | - | + | + | - | - |
| Valve 6 | - | - | - | + | + | + | + |
| Compressor | + | + | + | + | + | + | + |

*FIG. 7*

AUTOMATIC PORTABLE PNEUMATIC COMPRESSION SYSTEM

This application is a continuation application of U.S. patent application Ser. No. 09/413,968, filed Oct. 7, 1999 (now U.S. Pat. No. 6,494,852), which is a continuation-in-part of U.S. patent application Ser. No. 09/038,157, filed Mar. 11, 1998 (now U.S. Pat. No. 6,478,757), and is related to U.S. patent application Ser. No. 09/375,083 filed Aug. 16, 1999 (now U.S. Pat. No. 6,447,467).

BACKGROUND OF THE INVENTION

The invention relates to systems for applying compressive pressures against a patient's limb, specifically to a miniaturized, automatic portable ambulant system.

Various conventional compression devices are known for applying compressive pressure to a patient's limb. These types of devices are used to assist in a large number of medical indications, mainly the prevention of deep vein thrombosis (DVT), vascular disorders, reduction of edemas and the healing of wounds. Prior art devices are typically divided into two main segments: 1) a hospital segment, in which they are used mainly for the prevention of DVT in patients with high risk for developing the same, and 2) a home segment, in which they are mainly used to treat severe lymphedema. Although showing high clinical efficacy in treating the above clinical indication, prior art devices share the following disadvantages. First, they use the conventional main power supply (wall outlet), and thus impose total confinement on the patient during treatment. The pump unit is heavy (5–15 pounds), which makes it hard to maneuver and place in the vicinity of the patients. The pump unit is big and thus creates a storage problem, specifically in hospitals, in which a few units are stationed, usually in a special storage room. The sleeve is big and ungainly, and thus restricts the movement of the limb it encompasses and imposes an aesthetic discomfort. In addition, the use of multiple cells demands the use of multiple conduits (usually one for each cell) making the whole system more cumbersome and harder to maneuver. All of the aforementioned disadvantages result in poor patient and therapist (mainly nurses) compliant, resulting in that the devices are used for treatment only to the most severe cases of the medical indications described above.

Prior art devices need to be as big and use the conventional electrical outlets for the power supply as they all use the same basic shape of inflatable bladders for their sleeves. These devices use substantial amounts of fluid (usually air) in order to inflate the sleeve and create the desired pressure at a timely manner (between 0.25–10 seconds per chambre). As a consequence, the devices need a large compressor that require high current supply, which forces their connection to the electrical outlets for power supply. The same follows with respect to the need for relatively large components in the prior art devices, such as solenoids, air conduits etc.

The need for a small ambulant/portable aesthetic device has long been recognized by the industry, as evident from prior patents of leading companies in this field. Patents such as U.S. Pat. Nos. 5,795,312, 5,626,556, 4,945,905, and 5,354,260, as well as EP 0861652, and others, are concerned with using less air to inflate the sleeves, easier handling, especially with the connection of the pump unit to the patient bed, and all of the other disadvantages previously discussed.

A step in this direction was the introduction of foot pumps. Still, as scientists and engineers were fixed on improving the pumps (their flow rate, power consumption etc.) and not on improving the use of the pumped air (as described in the related U.S. patent applications of the applicant, that enables one to accomplish the same pressures in the same timely manner and the same therapeutic goals with about ¹/₁₀ of the volume of air prior art devices need), no major breakthrough in the size of the sleeve/ pump unit, its power source or mobility during use were accomplished until the present invention. A small, ambulant, portable device will achieve the following needs that prior art devices could not accomplish. First, patients will gain the freedom of movement without treatment interruption. Currently, patients in hospitals which are connected to prior art devices for 5 consecutive days following their operation cannot move from their beds unless treatment is interrupted, e.g., each time the patient needs to use the bathroom or move around, the nurse has to come unhook the patient from the device and afterwards reconnect the patient to the device. Home users of prior art devices (mainly patients suffering from acute lymphedema) have to confine themselves to one place during treatment and are restricted from basic mobility needs such as the use of bathroom, opening the door, etc. Second, it will be easy to use and handle. Currently, patients being discharged from the hospital are stopped from treatment by the device, although still considered under high risk for developing DVT, as the earlier described disadvantages (size, weight, mobility) of the devices makes them almost unsuitable for self use at home, especially when dealing with the elderly population. Nurses in the hospital are bothered by the need to connect and disconnect the many conduits most of the devices use and to carry and place the devices, from the storage room to the patient bed, back and forth. These are time consuming actions that need to be done whenever a new patient arrives, or if a fault arises in the device during operation or if the patient is moved for a short time from his or her bed. Third, it will eliminate the storage problem, with conventional devices there is a need for a storage room, mainly in the hospitals in which there are a few pump units and sleeves. Fourth, it will enable the user (mainly the home user) to get engaged in social activity during treatment. Conventional devices impose great aesthetic discomfort and thus restrict the home user from any social activity.

By achieving all the above needs, the new compression system will be suitable for use not only for severe cases of medical indication relating to the healing of wounds, reduction of edemas, vascular disorders and the prevention of DVT, but also to the mild cases, for whom, until now, the only alternate solution was the use of elastic stocking which are, clinically, inferior form of therapy compared with pneumatic compression systems.

SUMMARY OF THE INVENTION

In accordance with one embodiment of the invention, there is provided an improved system for applying pressure against a patient's limb. The system introduces a miniature, battery operated (rechargeable), ambulant pump unit, the size and weight of a personal radio, connected to an inflatable sleeve for use on a limb. The system can operate independently of a fixed power source as it uses small rechargeable batteries. The system can also operate while connected to a conventional electrical outlet, at the time of such operation or at any other time it is connected to the electrical outlet, the system will automatically recharge itself.

The system provides a pump unit that can be carried around while operating, connected to an aesthetic flexible inflatable sleeve that can easily be concealed, for example, under trusses. The sleeve has a plurality of cells arranged longitudinally along the sleeve from the distal part of the limb to which it is applied, to its proximal part. Each cell is subdivided into two or more longitudinally extending confluent compartments that are inflated and deflated essentially simultaneously. The system has means for intermittently inflating the cells during periodic compression cycles, and means for intermittently connecting the cells to an exhaust port.

In one aspect of the invention, the pump unit can be operated alternatively as a foot pump, calf pump or a simultaneous foot and calf pump. In another aspect, a combination of self operated relief valves and check valves can be used for the inflation and deflation of the sleeve cells, thus achieving additional compactness and lower power consumption of the pump unit, and uses only one air conduit between the pump unit and the sleeve. In yet another aspect, while the system is connected to a conventional electrical power outlet, the rechargeable batteries can be bypassed and recharged only if necessary, thus expanding their life expectancy. Yet in another aspect, the pump unit can use an accumulator in order to speed the time needed for the inflation of each cell.

Accordingly, the invention provides a system for applying compressive pressure to a limb in which the pump unit is small, light weight, ambulant and can operate independent of electrical power supply outlets, and utilizes a small flexible inflatable sleeve placed on a treated limb, thus enabling the freedom of movement of the treated person. The portability of the system allows for easy handling, placement in the vicinity of the patient, storage, and does not disturb the patient or surroundings during treatment.

In a further aspect of the invention, only one conduit is used from the pump unit to the inflatable sleeve, regardless of the amount of cells in the sleeve, thus greatly simplifying connection to the sleeve and improving patient compliance as numerous conduits usually restrict movement. The configuration enables reduction in the size of the pump unit, reduces current consumption of the pump unit and allows for longer independent operation. In addition, the system can utilize a connector between the pump unit and the conduits to the sleeve that is able to decide the needed treatment, thus eliminating the risk of choosing the wrong treatment, especially when more than one limb is treated and the treatment is asymmetric.

BRIEF DESCRIPTION OF THE DRAWINGS

FIG. 7 is a table of programmed control parameters for a control unit in the case of two three-chambered sleeves according to the invention;

DETAILED DESCRIPTION OF THE INVENTION

In the following, ,in embodiment of the invention will be described for use on the leg of an individual. However, it is to be understood that the invention is also intended for use on any body limb such as an arm, a foot, a part of a leg, arm or foot, and may be used on two or more limbs simultaneously.

Figure 1:
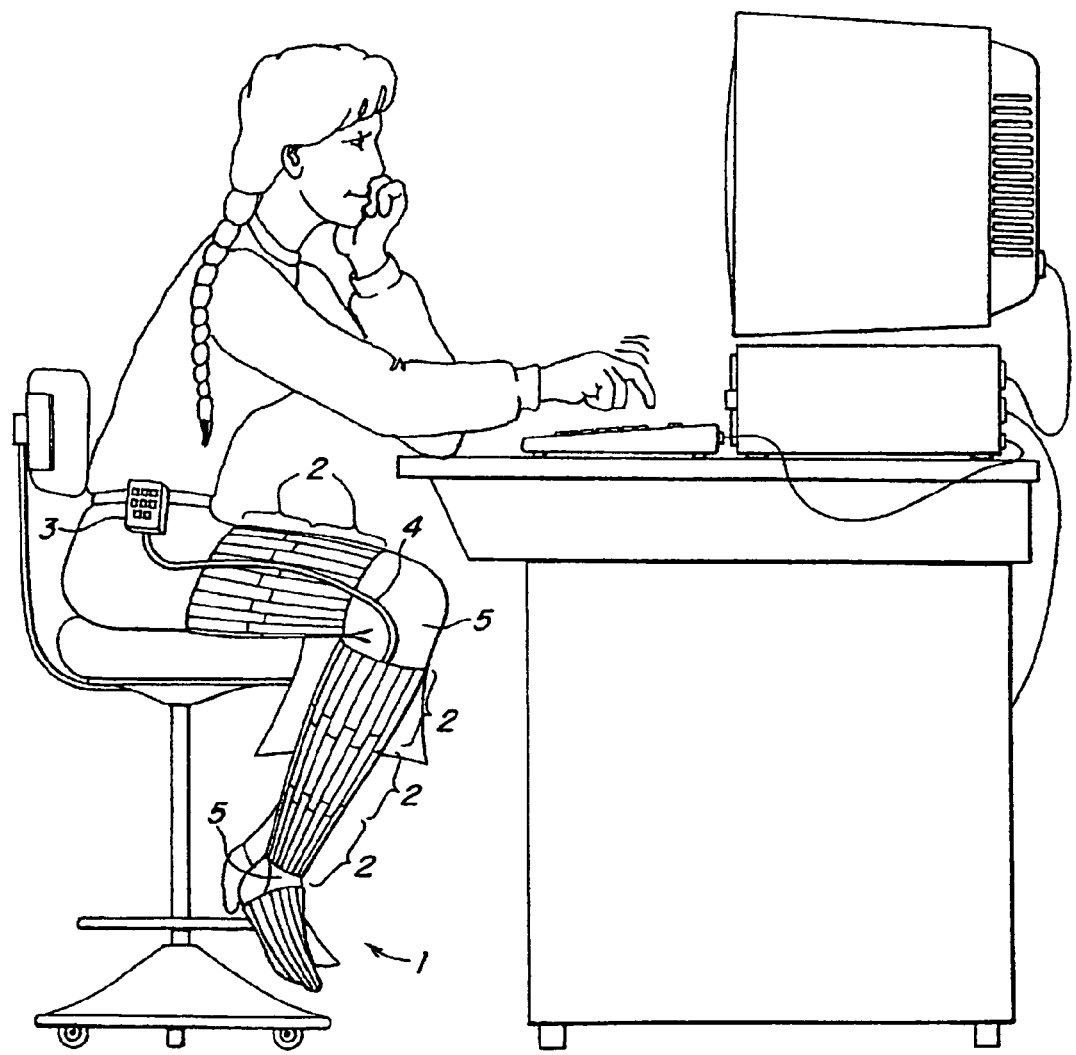
FIG. 1 is an illustration showing a massage sleeve according to the invention in use on the leg of a patient.

In FIG. 1, a patient is depicted wearing a massaging sleeve 1 of the invention on her leg while carrying out her routine duties. In FIG. 1, the trouser leg of the patient is cut away to reveal the sleeve. In practice, however, the sleeve remains concealed from view, and remains unnoticed even during operation when the cells are intermittently inflated. The sleeve 1 has an inner and outer surface composed of a durable flexible material and is divided into a plurality of cells 2 along its length and each cell is connected to the control unit 3 by a separate tube collectively labeled 4 in FIG. 1. Sections of the sleeve may be of non-inflatable elastic material 5, for example around the knee and ankle.

Figure 2:
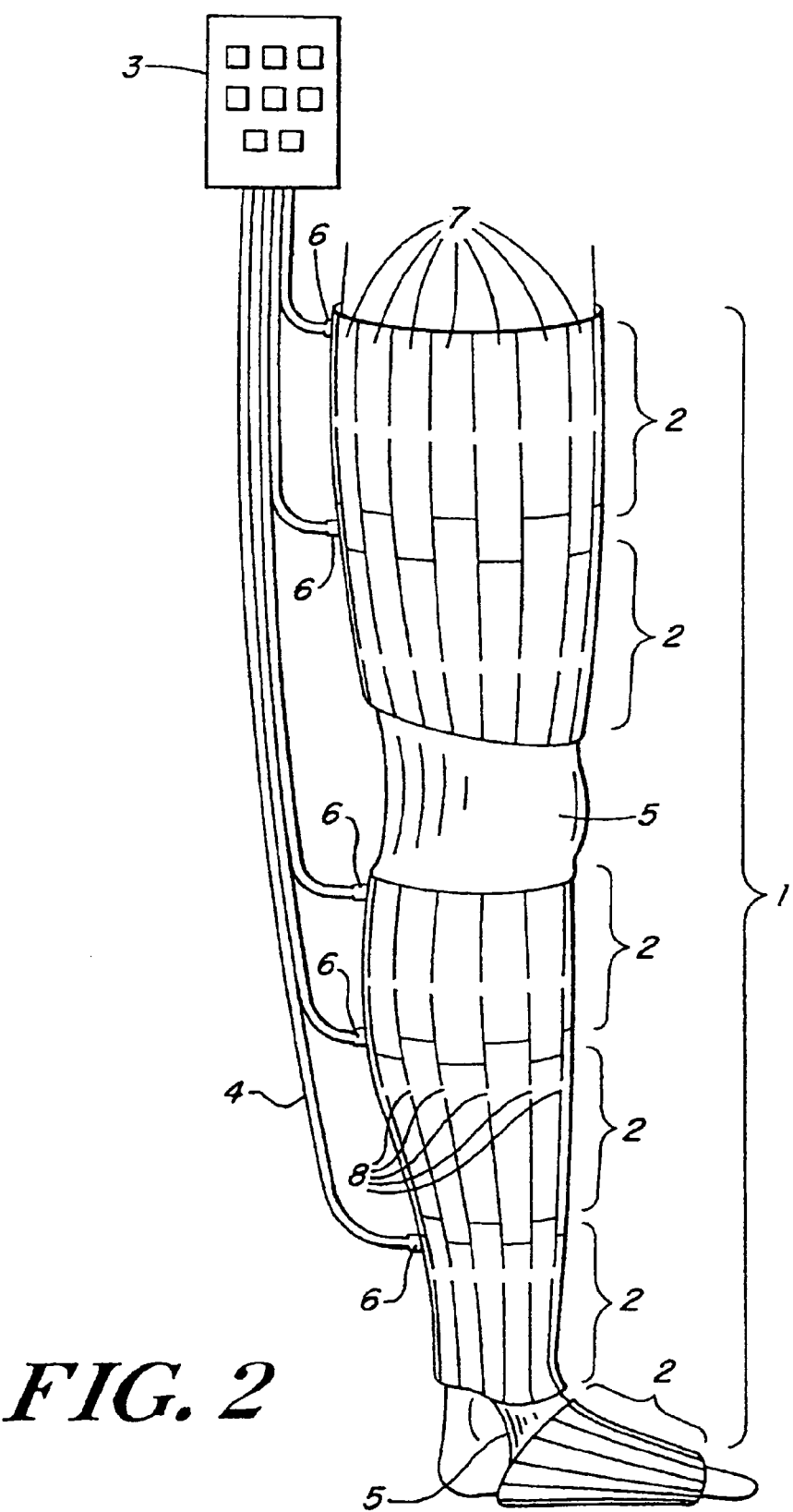
FIG. 2 is an illustration of a massage sleeve according to the invention mounted on the leg of a patient drawn to a larger scale.
Figure 3:
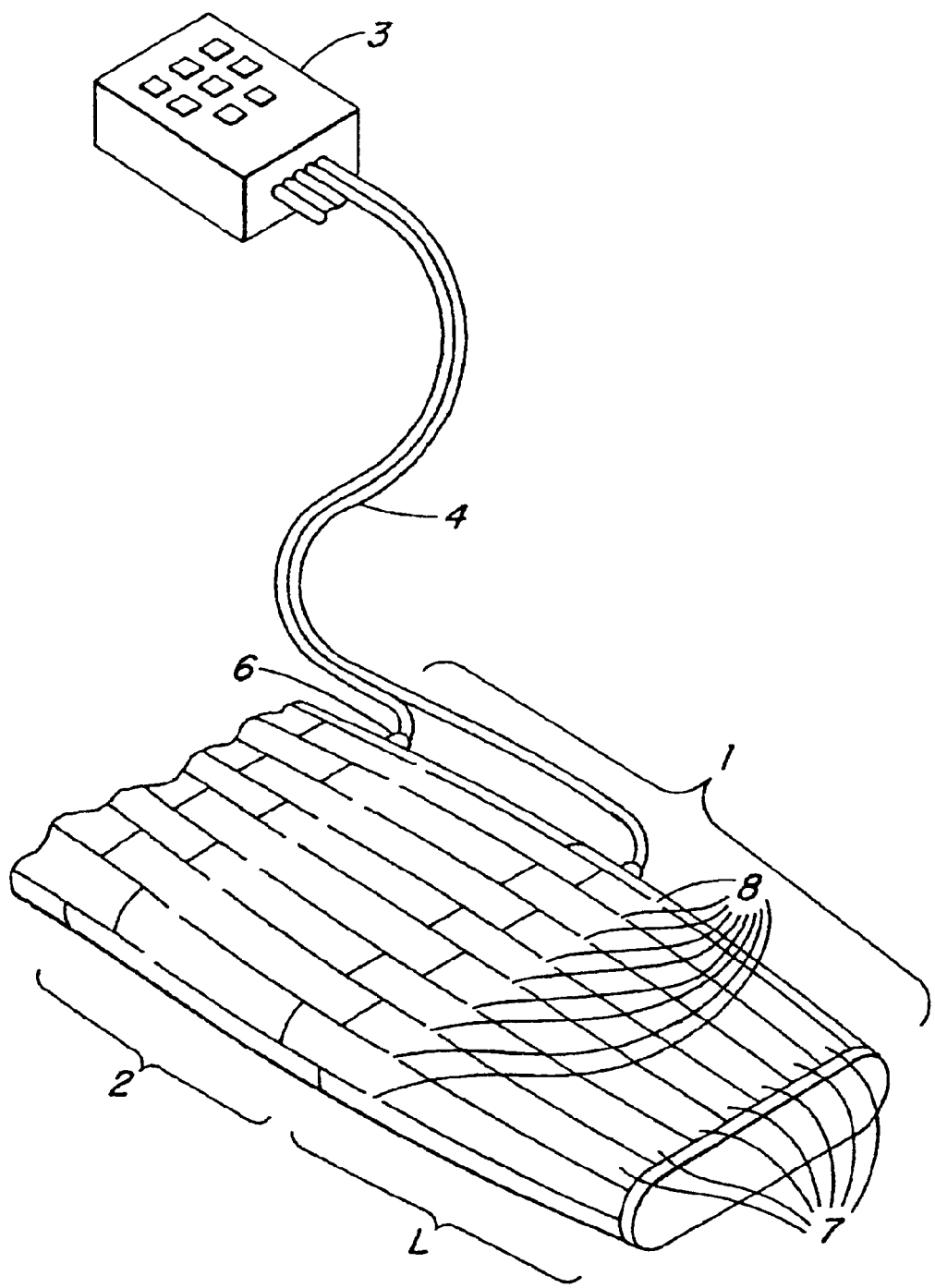
FIG. 3 is a partial perspective view of a massage sleeve according to the invention fitted with a control unit.

As can be seen in FIGS. 2 and 3, each cell has a fluid inlet opening 6 to which a hose 4 from the control unit 3 is attached. The control unit 3 contains a compressor capable of compressing and pumping ambient air into one or more selected cells in the sleeve via the hoses 4. The control unit 3 allows a temporo-spatial regime of inflation and deflation of the cells to be selected, e.g. a regime which generates peristaltic contractions of the sleeve so as to force fluids inside the limb towards the proximal end of the limb, or a regime which enhances the flow of the venous blood in the limb. The continuity of the peristaltic wave is enhanced by interdigitating the compartments of adjacent cells in the massaging sleeve as shown in FIGS. 2 and 3.

In accordance with the present invention, the cells are subdivided into a plurality of longitudinally extending compartments 7. The compartments are formed, for example, by welding the inner and outer shells of the massaging sleeve along the boundaries of the compartments. The compartments in a given cell are confluent due to perforations 8 in the seams between adjacent compartments so that all the compartments in the cell are inflated or deflated essentially simultaneously. Each compartment, when inflated, assumes essentially the shape of a cylinder having its axis parallel to that of the limb.

Figure 4A:
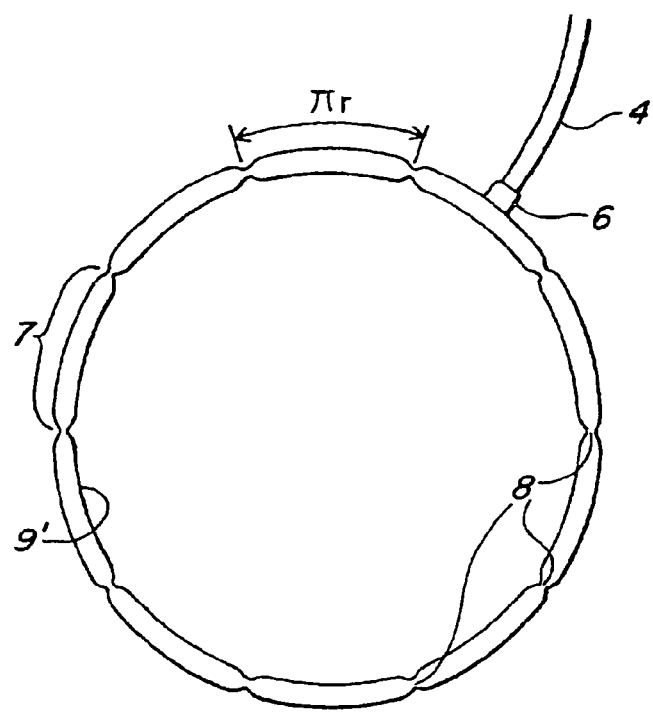
FIGS. 4A and 4B are cross-section views of a cell in the deflated and inflated states, respectively.
Figure 4B:
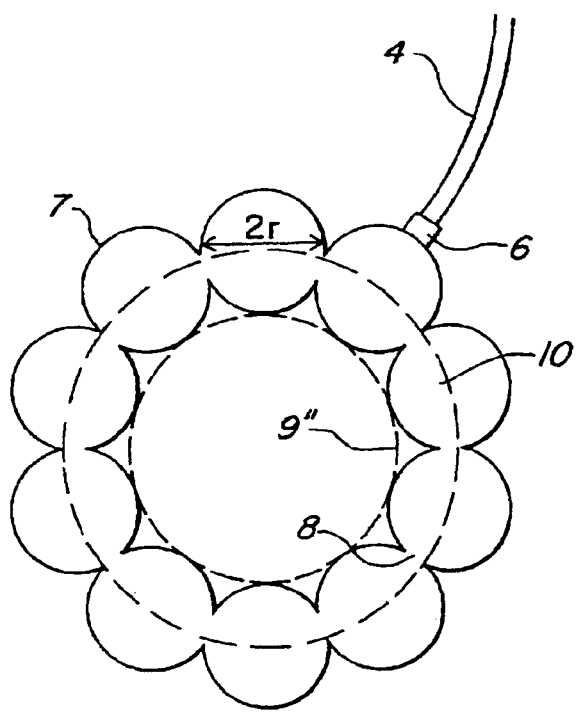

A cross-section of a deflated cell is shown in FIG. 4a, and FIG. 4b shows the same cross-section after inflation. Tile cell has been divided, by way of example, into ten identical compartments, it being self-evident that any other number of compartments may be used. If N is the number of compartments in a given cell, and r is the radius of an inflated compartment, then as can be seen in FIG. 4b the length of the circumference 10 that passes through the centers of the inflated compartments will be 2Nr, whereas the circumference 9' of the deflated cell is Nπr. The fractional decrease in the circumference upon inflation is thus $$\frac{N\pi r - 2Nr}{\pi Nr} = 1 - \frac{2}{\pi} = 0.36 \qquad (1)$$

The length of the inner circumference 9" of the inflated cell will be less than 2Nr so that the fractional decrease in the inner circumference upon inflation is thus greater than 0.36.

N and r are chosen so that πNr (the circumference of the deflated cell) corresponds to the original circumference of the limb segment contained within the lumen of the cell. The fractional decrease in the circumference of the cell upon inflation (0.36) causes a contraction of the cell whereby pressure is applied to the limb that, as follows from equation (1) above, is independent of N and r. Thus, by choosing N sufficiently large, and r correspondingly small, a sleeve is obtained having an inflated outer circumference not substantially larger than the original circumference of the limb. This is in contrast to prior art devices, which must have a circumference 36% greater than the initial circumference of the limb in order to achieve the same applied pressure as that produced by the present invention.

Letting now L be the length of a cell and C=Nπr, the initial circumference of the limb contained within the cell, it is readily appreciated from FIG. 4 that the initial volume of the limb contained within the deflated cell is $$V_D = \pi \left(\frac{C}{2\pi}\right)^2 L.$$

The final volume of the limb contained within the inflated cell is less than $$V_I = \pi \left(\frac{0.64 C}{2\pi}\right)^2 L = 0.41 V_D.$$

Inflating the cell thus leads to a decrease in the volume of the limb contained within the cell of about 59%. This represents the volume of fluid squeezed out of the limb, or the work performed by the sleeve. This is accomplished by inflating the compartments of the cell to a total volume of $$V_T = N\pi r^2 L = N\pi \left(\frac{C}{N\pi}\right)^2 L = \frac{C^2 L}{N\pi}.$$

In contrast to this, obtaining the same decrease in the volume of the limb by prior art methods requires inflating a cell to a final volume of $$V_F = \pi \left\{ \left(\frac{1.36 C}{2\pi}\right)^2 - \left(\frac{0.64 C}{2\pi}\right)^2 \right\} L = \frac{C^2 L}{2.8 \pi}.$$

Thus, when the number of compartments in the cell of the present invention is at least 3, the volume to which the cell must be inflated is less than that of prior art devices. Moreover, by choosing N sufficiently large, a decrease of 59% in the volume of the limb can be obtained by inflating the cell to an arbitrarily small total volume. For example, when N=30, the total volume of the inflated cell is less than one-tenth of the volume of the inflated cell of the prior art devices. This allows a much smaller compressor to be used than is possible with prior art sleeves, thus permitting the patient to be ambulatory while being treated by the invention.

It is noted that a sleeve according to the invention, e.g. such as sleeve 1 in FIGS. 1 and 2 or a smaller sleeve covering only a portion of a limb, may be used for immobilization of a fractured bone in a limb.

Figure 5:
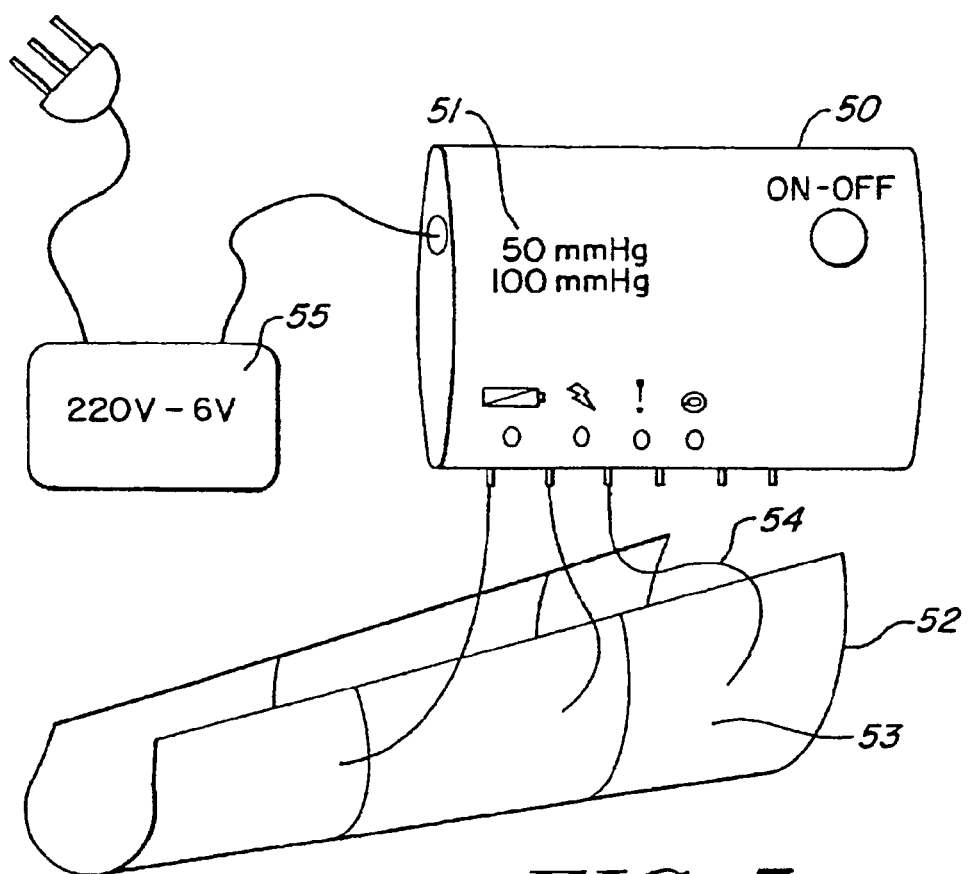
FIG. 5 is a block diagram of a pneumatic pressure system according to the invention.

FIG. 5 is a block diagram of a pressure system 50 includes a pump unit 51, which utilizes an electrical power supply/charger unit 55, such as a conventional electrical wall outlet, and an inflatable sleeve 52. The sleeve has a plurality of cells 53 arranged longitudinally along the sleeve. The pump unit and the sleeve are connected by conduits 54. The sleeve is placed over a limb and inflated, from its distal part to its proximal part in some desirable cyclic manner by the pump unit, thus creating the desirable pressure cycle on the limb. It will be appreciated that the system can include at least one or more flexible sleeves 52 with single or multiple inflatable cells 53 adapted to be in contact with the body part to be treated. The best selection of a sleeve is one that requires small volume change to exert the needed pressure.

Figure 6:
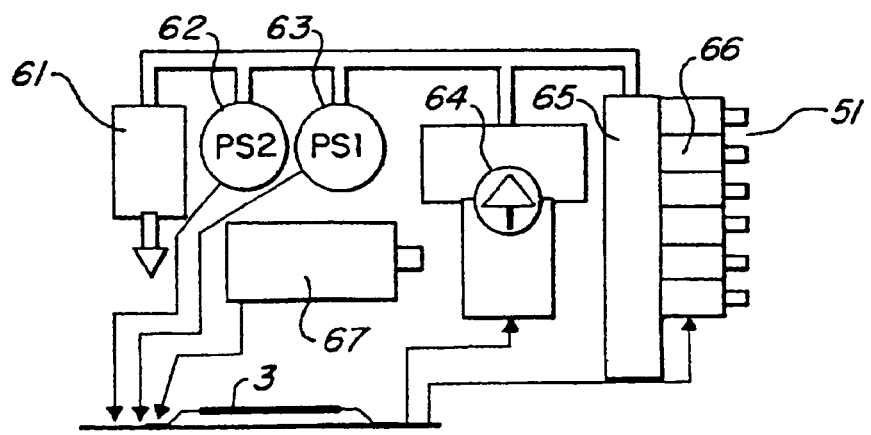
FIG. 6 is a schematic block diagram of a pump unit that corresponds to further details of the pump unit of FIG. 5.

FIG. 6 is a schematic block diagram of a pump unit 60 that corresponds to further details of the pump unit 51 of FIG. 5. It will be appreciated that the thick interconnecting lines represent pneumatic connections, while the thin interconnecting lines represent electrical connections. The pump unit 60 includes an independent source of energy, such as a rechargeable battery pack 67, which enable the pneumatic device operation without a fixed connection to a main power outlet. The batteries can be bypassed and the device is able to operate for longer times, and the batteries can be recharged at the same time, while it is connected to the main power supply with the aid of the charger 55.

A source of compressed air, such as a compressor 64, is powered by the batteries or the main electrical outlet, and connected to the sleeve or sleeves 52 by pneumatic conduits 54. A control unit 68 is adapted to receive inputs from the operator and from pressure sensors 62, 63. The control unit serves to read and control the operation of the compressor 64 and to control the cyclic inflating and deflating of the sleeve 53. The control unit also controls the operation of solenoid valves 66 and pressure relief valve 61, which receive and distribute the flow to the different cells 53 with the aid of a manifold 65, to enable the sequential inflating and deflating of the multi-segmented sleeve's cells 53.

The use of miniaturized components like the compressor 64 and solenoid valves 66, together with the miniature accessories, results in small power consumption that enables the operation of the pneumatic device on batteries, while maintaining small dimensions and light weight of the operating unit. The use of a sleeve 53 with a small-inflated volume will improve the obtained results of the operation unit for better clinical operation and results.

The operation of the system of the invention will now be described. Pneumatic devices apply cyclic sequential pressure on a body's legs or arms. The cyclic sequential pressure is applied on the treated parts of the body by inflating and deflating each cell 53 of the sleeve 52 at a predefined timing. While being inflated, the multi-chambered segmented sleeve 52 should be encircling the part of leg to be treated. While the sleeve is inflated, a local pressure is applied at the contact area between the sleeve and the body.

The control unit 68, which can be software based, controls the operation of the compressor 64 and solenoid valves 66. The control unit can be programmed to achieve any desired inflating and deflating sequence and timing including delay intervals, in accordance with clinical application. For example, in the case of two three-chambered sleeves (six solenoid valves), the controller can be programmed to operate in accordance with the table of parameters for the control unit shown in FIG. 7.

Each time interval from the table (T1, T2, . . . , T7) can be changed independently. The pressure level of the treatment can be controlled by the patient or the therapist. An example of an exemplary operation of the system in accordance with the invention is illustrated in the flowchart of FIGS. 8A–8E, describing self-checks and error detection processes, as well as normal operation of the system.

Figure 8A:
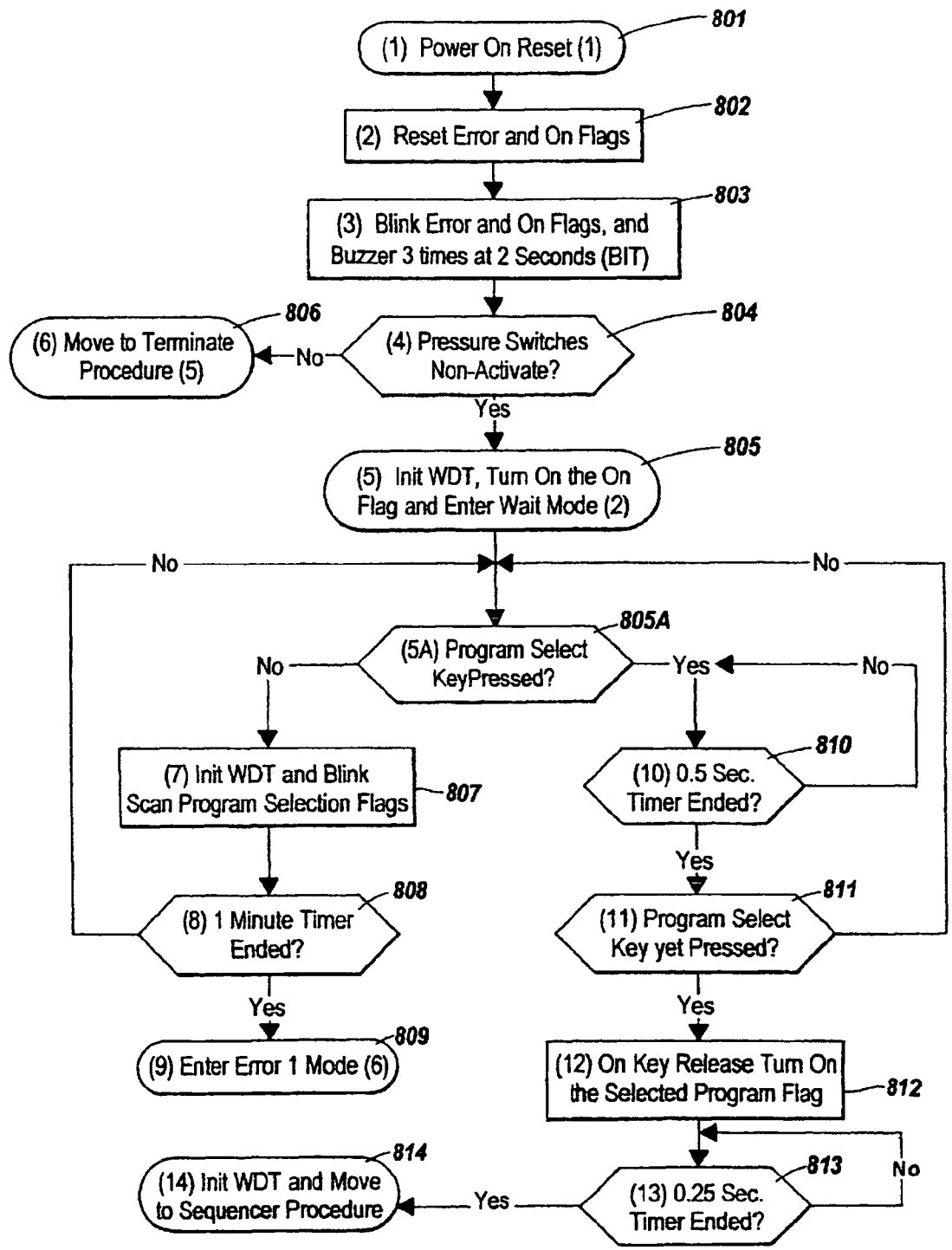
FIGS. 8A–8E illustrate a flowchart of an exemplary operation of the system in accordance with the invention.

In FIG. 8A, the operation begins with on power reset (cold or hot) (801). The system initializes a built in test (BIT) procedure which checks the display, the buzzer and the pressure sensors (802,803,804). If the sensors are found to be activated at this stage, the system holds (through termination procedure ((806) and 837–840)). If the BIT ends correctly, the system resets the watch dog timer (WDT) which prevents locking of the system and turns on the ON Flag (on the display) (805), and enters the WAIT mode, where it waits for a program (treatment) selection.

A WAIT procedure starts at step (805A) where keys are checked. If keys are not pressed, the system blinks the program flags at the display (807). If more than 1 minute has passed without any key pressed (808), the system enters error mode 1 ((809) and (841–845)). Restarting the system is the only way to go back from this mode of operation.

If a program key is pressed, the system de-bounces for 0.5 sec and then checks the keys again (810). If no key is pressed after the de-bounce time, the system returns to the start of the WAIT procedure. If a key is pressed after the de-bounce time, the system turns on the selected program flag (on the display) (812), and after a 0.25 sec delay (813) resets the WDT and starts the sequencer procedure (815).

Figure 8B:
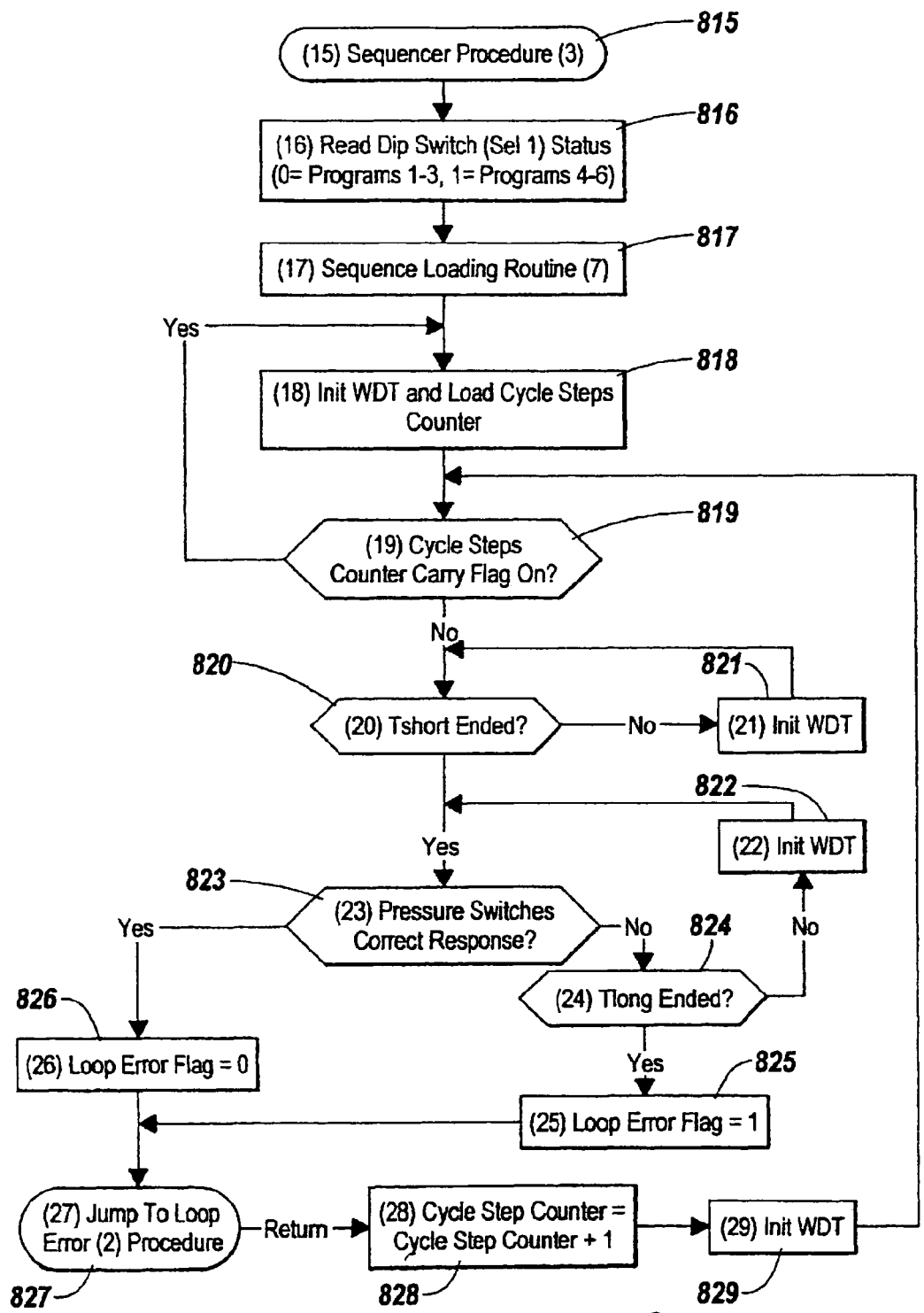

With reference now to FIG. 8B, at the first stage in the procedure reads the program group (Dip Switch) on the board (816). Note that this switch is hidden from the user. At that time, the requested treatment program is well defined, and the system starts loading data (817). This data can be loaded from two different sources, one a preloaded sequence which is part of the content of the system controlling processor. The second source is the sleeve itself, equipped with a special connector and internal memory, which enables special treatments to be supported (plug and play procedure) (Detailed data of this procedure provided in (864–868). After the sequence has been loaded, the WDT resets again, and data is entered to the cycle counter (which holds the sequence data, as previously supplied) (818).

The sequence starts by moving data to the pump and the valves and continues with a short period delay before checking the pressure sensors (820). Until this delay is finished, the system waits (820–821). After that, the system checks the sensors (823). If the sensors do not react correctly until the max available time (823, 824, 822), a sequence step error is stored (825). Later on, those errors will be analyzed (830–836). If the sensors reacted correctly at the time window, a non-error flag is stored (826). The system branches to the error analyzing procedure (827 and 830). If the system returns (not enough errors to hold), the cycle step counter advances (828, 829) and the next step starts (819).

Figure 8C:
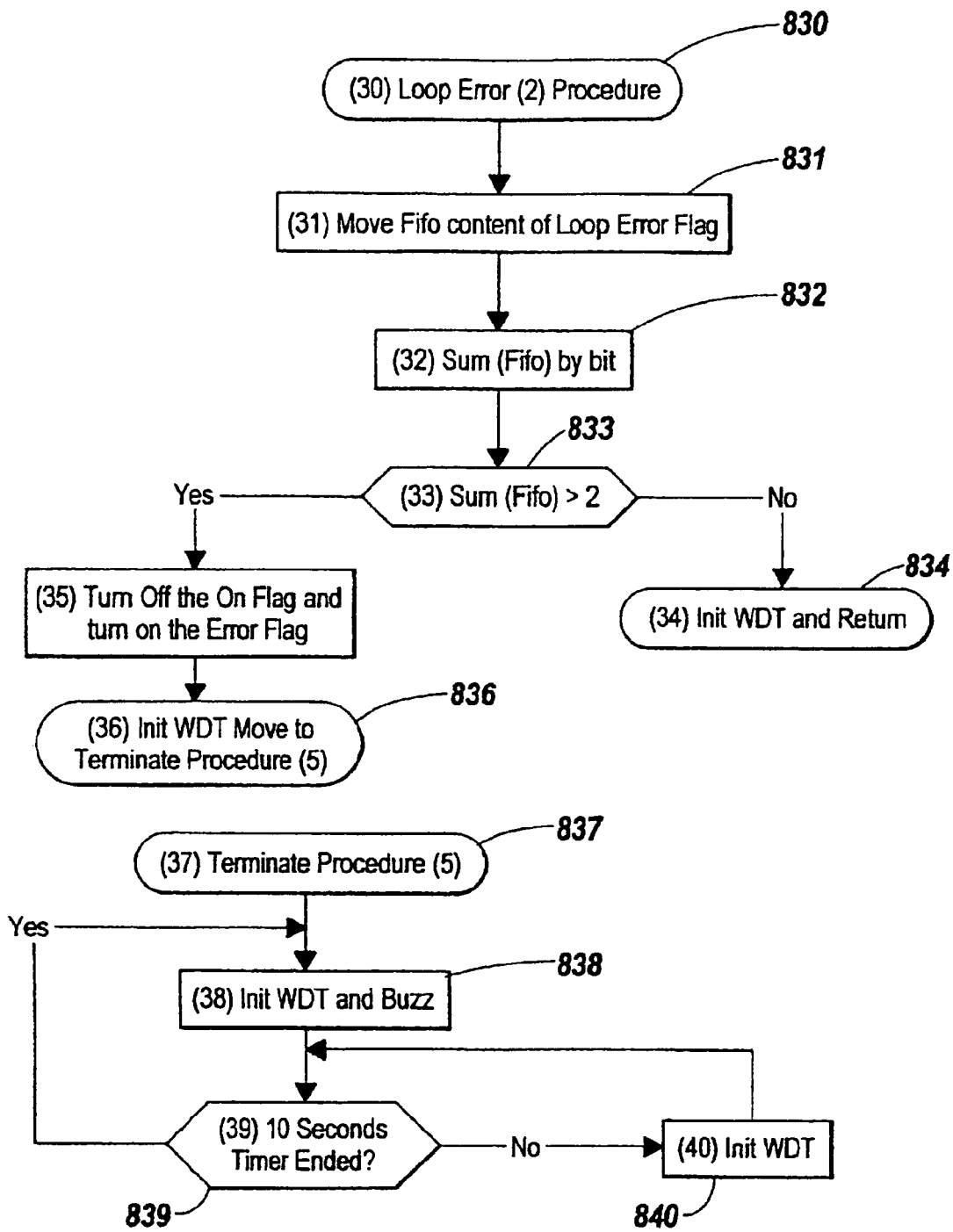

In FIG. 8C, the error analyzing procedure (830) starts by storing the last calculated error flag in a 24 bits long FIFO register (831). The number of errors in the register is counted (832) and if the number exceeds 2, i.e., 3 errors in 24 steps, the system starts a HOLD procedure (835, 836). The HOLD procedure starts turning off the ON flag on the display, and turning on the ERROR flag, and then proceeds to the termination procedure (837–840).

If the number of errors does not exceed 2, the system initializes the WDT and returns to step (827) and continues. The termination procedure is as follows. The termination procedure starts at step (837) by operating the buzzer (838), and waits 10 seconds (839, 840) before re-operating the buzzer.

Figure 8D:
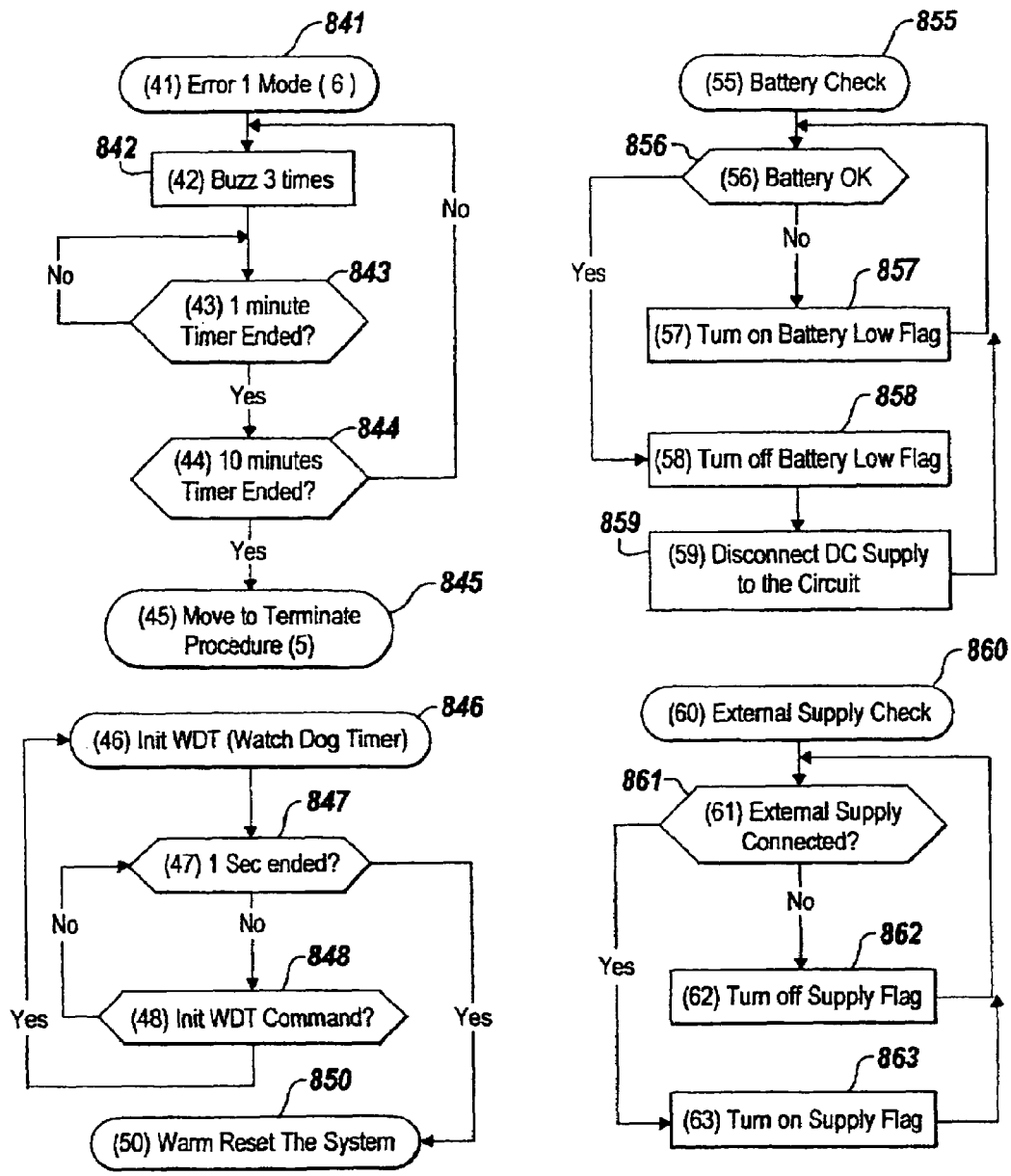

In FIG. 8D, an error 1 procedure is described. The error 1 mode starts at step (841), operates the buzzer 3 times, waits 1 minute (843), and if time from start (841) did not exceed 10 minutes (844), it repeats the buzz procedure. If yes, the system moves into the termination procedure (845 and 837).

The WDT procedure starts at step (846), by resetting and re-programming the WDT counter to a 1 second interval. If, within this time interval (847) no WDT initialization pulse arrives (848), the WDT will reset the whole system (850).

A battery check procedure (855–859) are hardware mechanisms that operate independently, without the software. An external supply check procedure (860 to 863) are hardware mechanisms that operate independently, without the software.

Figure 8E:
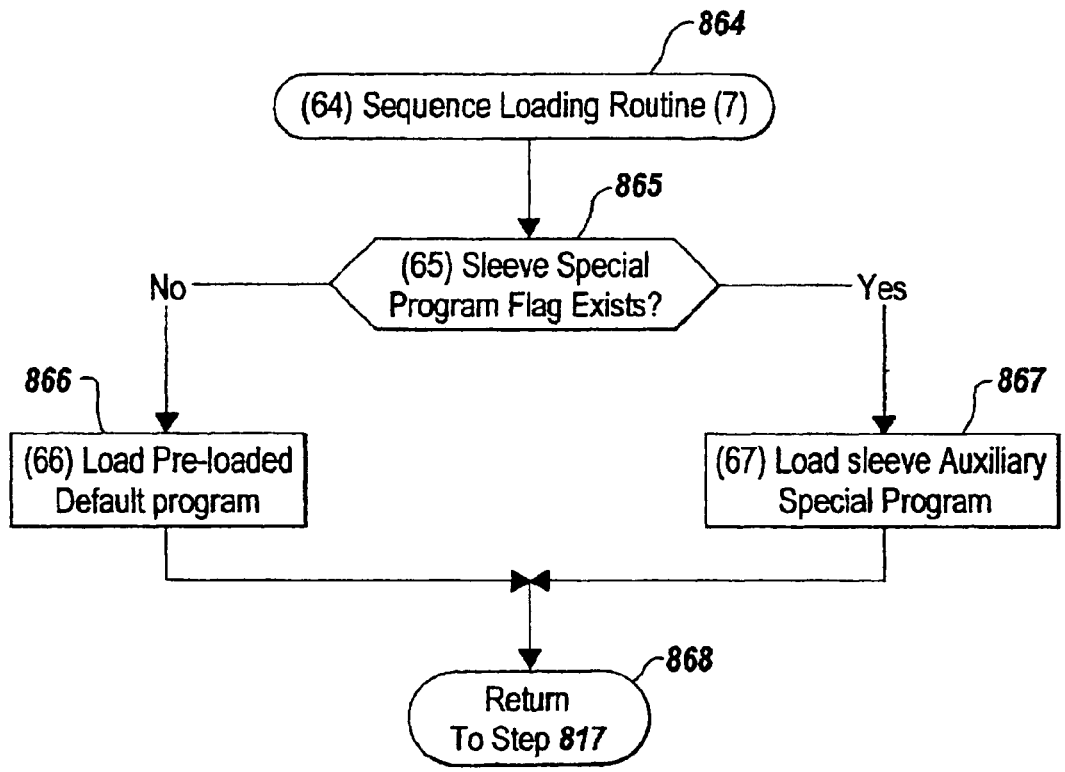

With reference to FIG. 8E, an internal/external sequence loading procedure is shown. This unique function of the system enables use of both pre-loaded treatment sequences in the pump unit processor (internal) and to receive new treatments parameters from an electronic unit placed within the sleeve's connector (external). The sleeve connector to the system includes, together with the air tubes, an electronic memory and/or processing device, the presence of which is detected by the system. Detecting such a device causes the system to load the sequence data from the sleeve memory, and not from the pre-loaded memory which is part of the processor. This is referred to conventionally as a "plug and play" mechanism. The procedure starts at step (864), then the system checks the presence of an intelligent sleeve (865). If one exists, the sequence is loaded from the intelligent sleeve (867). If no intelligent sleeve is detected, then the pre-loaded sequence is loaded (866). Finishing loading the system causes the program to return to the next step (817).

Figure 9:
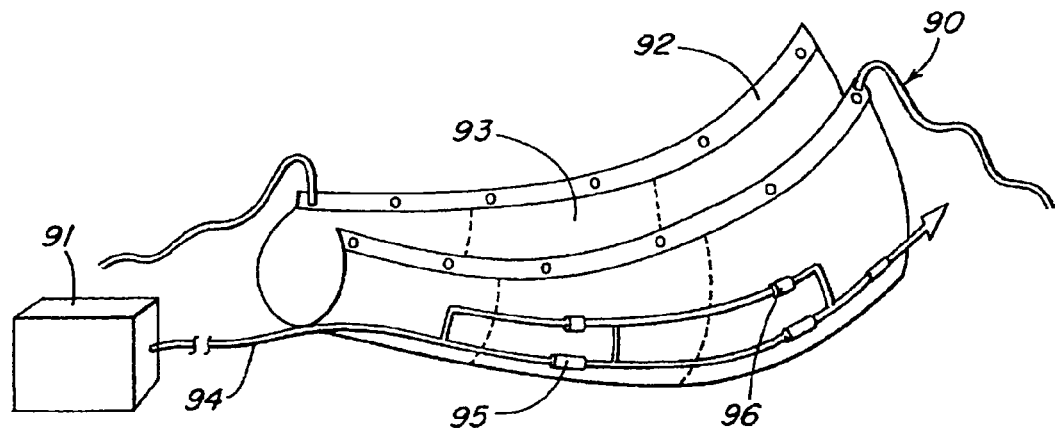
FIG. 9 is a block diagram of an alternative embodiment of a pneumatic pressure system according to the invention.

Additional miniaturization and mechanical simplification of the portable ambulant pneumatic pressure system of the invention can be achieved by introducing self-operated relief valves replacing the controlled operated solenoid valves. Another embodiment of a portable pneumatic pressure system 90 of the invention is illustrated in FIG. 9. The system includes a pump unit 91, at least one inflatable sleeve 92 with a single or multiple inflatable cells 93 adapted to be in contact with the body part to be treated.

An independent source of energy, for example rechargeable batteries, is provided which enables the pneumatic operation without a fixed connection to a main electrical power outlet. The batteries can be bypassed and thus system can operate for longer time periods while it is connected to the main power, and the batteries can be recharged at the same time.

Figure 10:
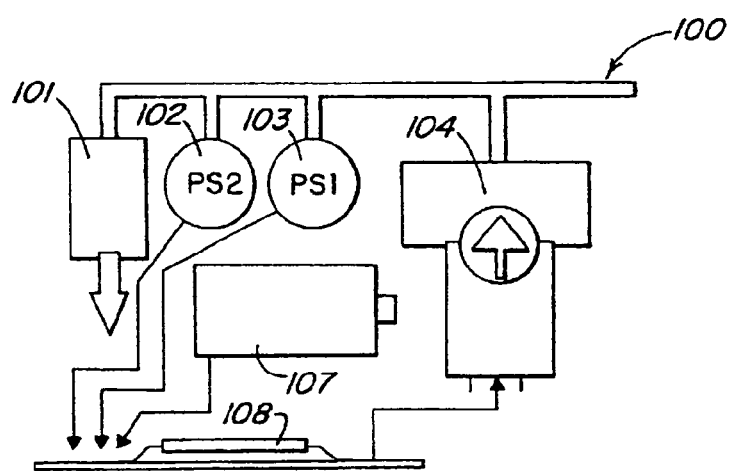
FIG. 10 is a schematic block diagram of a pump unit that corresponds to further details of the pump unit of FIG. 9.

FIG. 10 is a schematic block diagram of a pump unit 100 that corresponds to further details of the pump unit 91 of FIG. 9. It will be appreciated that the thick interconnecting lines represent pneumatic connections, while the thin interconnecting lines represent electrical connections. The pump unit 100 includes an independent source of energy, such as a rechargeable battery pack 107, which enable the pneumatic device operation without a fixed connection to a main power outlet. The batteries can be bypassed and the system is able to operate for longer times, and the batteries can be recharged at the same time.

A source of compressed air, such as a compressor 104, powered by the batteries or by the main power, is connected to the sleeve 92 or sleeves by one single pneumatic conduit 94, which enables inflating and deflating the cells 93. The compressor in this embodiment, can enable the inverted flow to deflate the cells of the sleeve. It is possible to use a rotary compressor or to enable the inverted deflating flow by means of a valve which may be solenoid operated and which is actuated by a control unit 108, or alternatively a pneumatic operated normally open valve can be used. The valve will be kept closed using the pressure of the compressor while the compressor is energized, and will open by itself when the compressor is stopped.

The control unit 108 is adapted to receive the operator's commands and control the operation of the compressor to control the cyclic inflating and deflating of the sleeve. Solenoid valves are replaced, in this embodiment, by self-operated relief valves 95, one with each chamber. The compressor is directly connected to the first cell. Each cell is connected to the next, one through a relief valve to regulate the pressure and maintain a pressure gradient. Each relief valve (except the last one) is bypassed with a conduit section including a check valve 96 to allow deflating of the cell. The last relief valve is open to the atmosphere, thus limiting the maximal pressure in the cells.

The control unit 108 controls the operation of the compressor 104 to inflate the first cell 93. The pressure in the first cell is built-up, and when it gets higher than the first relief valve 95 opening pressure, the second cell starts to be inflated. The third cell is inflated while the pressure in the second cell reaches the burst pressure of the second relief valve. The inflating process will continue in the same manner until the last cell is inflated. When the pressure in the last cell bursts the last relief valve, air will commence to flow out to the atmosphere preventing an uncontrolled pressure build-up inside the sleeve. When the operating interval of the compressor terminates, the controller de-energizes the compressor and enables all of the cells to be deflated simultaneously.

By using self-operated relief valves instead of the controlled solenoid valves, the system in accordance with the invention will be smaller, lighter, have longer independent operation (as power consumption is reduced), and will be more cost effective. There will be a decrease in the operational flexibility because the relief valves are self-operated, and the controller can no longer control the inflating sequence of the cells.

The automatic portable ambulant pneumatic pressure system of the invention is capable of treating more than one part of the body by connecting more than one sleeve to the pump unit. Sometimes, for medical reasons, the treatment is not symmetric on the body, i.e., treatment applied on the left calf and the right foot, and a different treatment is required in each sleeve. The sleeves used for the different treatments differ from each other by appearance because they are designed to operate on a different part of the body. They can also differ with the number of chambers and the connected conduits. The pump unit has the capability to operate each one of the sleeves with the appropriate medical treatment cycle.

The pump unit can identify the combination of treatments without requesting information from the operator. The operator will select the right sleeves and connect them to the pump unit. That will be sufficient for the system to identify the required treatment cycles and will prevent the possibility of mismatched input to the system by selecting a treatment, which is not suitable to the fixed sleeves or vice versa.

The control unit, within the pump unit, will read the input information about the required treatment by reading the coding of the sleeves connectors. While starting any new treatment cycle, the control unit will start the treatment by a quick identification of the type of sleeves connected and will apply the appropriate operating cycle. The coding of the sleeve connectors can be made by state of the art mechanical or electro-mechanical components. It is also possible to store the required treatment parameters on the sleeve's connector according to the sleeve's projected treatment. On start-up of the system, the data will be transferred to the pump unit by way of state of the art technology, and the treatment cycle will be compatible to the selected sleeve. The therapist will be able to program the sleeve's parameters to fit the treatment to the patient.

Figure 11:
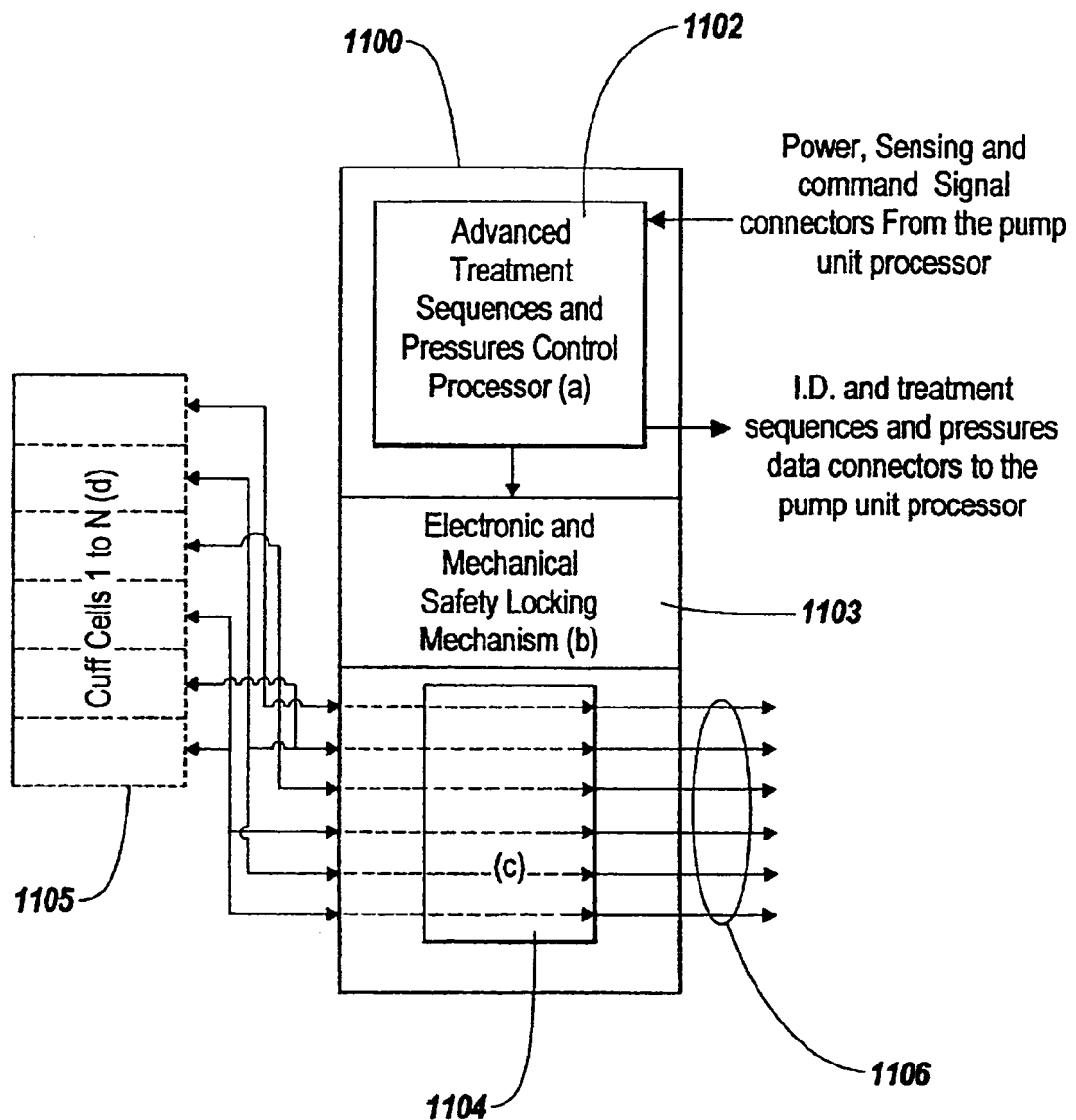
FIG. 11 is a simplified functional block diagram of an exemplary connector assembly in accordance with the invention.

FIG. 11 is a simplified functional block diagram of an exemplary embodiment of a connector assembly 1100 for an associated sleeve 1105 in accordance with the invention. The assembly 1100 includes an electronic memory and/or control processor unit 1102 that is capable of detecting and transmitting electronic signals. When connected to a pump unit and on power reset of the pump unit, the processor unit, which can be part of the conduits of the sleeve, receives DC power and sends back an identification signal which initiates the communication procedures. The treatment data will be loaded to the pump unit. The second phase of this operation is to lock the cuff of the sleeve, with an electro-mechanical safety locking mechanism 1103. This operation is done for safety reasons, to prevent undesired release of the cuff, during normal operation.

Another feature is that a pressure sensors array 1104 measures the pressure at the end of each pressure line 1106. The data collected at this stage is transmitted, via the processor unit 1102, to the processor in the pump unit, in order to evaluate the status of the system. The sleeve 1105 has several cells that can be independently inflated by the pump unit. The number of cells in the sleeve can vary, according to desired treatments.

Although the present invention has been shown and described with respect to several preferred embodiments thereof, various changes, omissions and additions to the form and detail thereof, may be made therein, without departing from the spirit and scope of the invention.

What is claimed is:

1. A device for applying pressure to a body limb having a primary axis, comprising:

first and second inflatable cells, each of the first and second cells including at least three intra-cell compartments; said intra-cell compartments being confluent, each compartment being elongated along a primary axis of a body limb and being substantially rectangular in shape when deflated and substantially cylindrical in shape when inflated, cylindrical axes of the inflated compartments substantially aligning with the primary axis of the limb, the first and second cells being longitudinally adjacent each other, and arranged coaxially with respect to the primary axis of the limb, the first and second cells being intermittently inflatable to apply pressure to the limb, wherein the inflatable cells each comprise inner and outer shells of durable flexible material, said inner and outer shells being bonded together to form a perimetric cell bond to define the inflatable cell therebetween, said inner and outer shells being further bonded together to form compartmental bonds within the perimetric cell bond to define the plurality of intra-cell compartments, wherein the perimetric cell bond includes upper and lower perimetric cell bonds extending substantially in a lateral direction, and left and right perimetric cell bonds extending substantially in the longitudinal direction, and wherein the compartmental bonds partly extend between the upper and lower perimetric cell bonds, wherein the compartmental bonds include perforations to allow for confluent air flow between compartments within a cell, neighboring compartments along a lateral axis sharing a common border and being spatially fixed relative to each other, such that upon inflation of a cell, the cell becomes circumferentially constricted, the first and second cells being non-confluent such that the first and second cells are separately inflatable;

means for laterally coupling outermost compartments so as to form a sleeve substantially cylindrically;

inflating means for intermittently inflating the first and second cells; and control means for determining a treatment specificity of each cell and for determining a timing sequence for inflating of each cell based on the determined treatment specificity of each cell;

said sleeve having a center point circumference of $N\pi r$ when the cell is deflated and a center point circumference of $2Nr$ when the cell is inflated, where N is the number of compartments in the cell, and where r is the cross-sectional radius of each compartment when inflated, the center point circumference being a line passing through each center point of each adjacent intra-cell compartment of said inflatable cell;

said compartmental bonds of said intra-cell compartments, during inflation, being drawn towards each other to decrease a distance therebetween and towards the center point of said intra-cell compartments to decrease a distance therebetween, so as to provide for circumferential constriction.

2. The device of claim 1, wherein the center point circumference is decreased upon inflation by about 36%.

3. The device of claim 1, wherein the bond comprises a weldment.

4. The device of claim 1, wherein adjacent compartments are contiguous.

5. The device of claim 1, wherein the perforations are located adjacent the perimetric cell bond.

6. The device of claim 1, wherein the perforations are located between compartmental bonds extending from the upper and lower perimetric bonds.

7. The device of claim 1, further comprising a fluid inlet to provide for inflation and deflation of the cell.

8. An automatic portable ambulant system for applying pressure to a body limb, comprising:

a sleeve including first and second inflatable cells, each of the first and second inflatable cells including at least three intra-cell compartments;

said intra-cell compartments being confluent, each compartment being elongated along a primary axis of a body limb and being substantially rectangular in shape when deflated and substantially cylindrical in shape when inflated, cylindrical axes of the inflated compartments being adapted to substantially align with the primary axis of a body limb, the first and second cells being adjacent to each other and being adapted to be arranged coaxially with respect to the to primary axis of a body limb, the first and second cells being intermittently inflatable to apply pressure to a body limb, wherein each inflatable cell comprises inner and outer shells of durable flexible material;

said inner and outer shells being bonded together to form a perimetric cell bond, said perimetric bond defining outer boundaries of an inflatable cell and boundaries between the inflatable cells, said inner and outer shells being further bonded together to form compartmental bonds, said compartmental bonds defining boundaries between intra-cell compartments, wherein the perimetric cell bond includes upper and lower perimetric cell bonds extending substantially in a lateral direction, and left and right perimetric cell bonds extending substantially in the longitudinal direction, and wherein the compartmental bonds partly extend between the upper and lower perimetric cell bonds, wherein the compartmental bonds include perforations to allow for confluent air flow between intra-cell compartments within a cell, the first cell becoming circumferentially constricted when the first cell is inflated, the second cell becoming circumferentially constricted when the second cell is inflated, the first and second cells being non-confluent such that the first and second cells are separately inflatable;

means for laterally coupling the outermost intra-cell compartments within a cell so as to form said sleeve substantially cylindrically;

a portable hand-held pump unit for intermittently inflating any one or more selected cells of the sleeve via a conduit, said pump unit including a control unit for determining a treatment specificity of each cell and for determining a timing sequence for inflating of each cell based on the determined treatment specificity of each cell;

said sleeve having a center point circumference of $N\pi r$ when the cell is deflated and a center point circumference of $2Nr$ when the cell is inflated, where N is the number of compartments in the cell, and where r is the cross-sectional radius of each compartment when inflated, the center point circumference being a line passing through each center point of each adjacent intra-cell compartment of said inflatable cell;

said compartmental bonds of said intra-cell compartments, during inflation, being drawn towards each other to decrease a distance therebetween and towards the center point of said intra-cell compartments to decrease a distance therebetween, so as to provide for circumferential constriction.

9. The system of claim 8, wherein said pump unit is battery operated.

10. The system of claim 9, wherein said pump unit comprises a rechargeable battery.

11. The system of claim 8, wherein said pump unit comprises an air compressor.

12. The system of claim 8, wherein said conduit comprises a single tube for delivering fluid to said sleeve.

13. The system of claim 8, wherein said conduit comprises means for indicating to said control unit the treatment specificity of each cell.

14. The system of claim 8, wherein said sleeve comprises at least one self-operated valve.

15. A device for applying pressure to a body limb having a primary axis, comprising:

first and second inflatable cells, each of the first and second inflatable cells including at least three intra-cell compartments;

said intra-cell compartments being confluent, each compartment being elongated along a primary axis of a body limb;
said first and second inflatable cells being adjacent each other and arranged coaxially with respect to the primary axis of the limb when engaged with a limb;
said first and second inflatable cells each including inner and outer shells of durable flexible material;
said inner and outer shells being bonded together to form a perimetric bond about a perimeter of the inflatable cell, said perimetric bond defining the inflatable cell as a volume between said inner and outer shells and within the perimetric bond;
said inner and outer shells being further bonded together to form a plurality of is compartmental bonds within the inflatable cell bond, said plurality of compartmental bonds defining the three intra-cell compartments
said perimetric cell bond including first and second perimetric cell bond portions, said first and second perimetric cell bond portions being substantially parallel thereto, wherein a portion of said compartmental bonds partly extending between said first and second perimetric cell bond portions;
said compartmental bonds extending between said first and second perimetric cell bond portions including perforations to allow for confluent airflow between adjacent intra-cell compartments within a cell;
said adjacent intra-cell compartments within a cell being spatially fixed relative to each other such that upon inflation of said adjacent intra-cell compartments within the cell, the cell becomes circumferentially constricted;
said first and second inflatable cells being non-confluent such that that said first and second inflatable cells are separately inflatable;
means for laterally coupling outermost compartments so as to form a substantially cylindrical sleeve;
inflating means for intermittently inflating said intra-cell compartments of said first and second inflatable cells; and
control means for determining a treatment specificity of each cell and for determining a timing sequence for inflating of each cell based on the determined treatment specificity of each cell;
said sleeve having a first intra-cell compartment center point circumference when said intra-cell compartments are deflated and a second intra-cell compartment center point circumference when said intra-cell compartments are inflated, said second intra-cell compartment center point circumference being less than said first intra-cell compartment center point circumference so as to provide for circumferential constriction, said first and second intra-cell compartment center point circumferences, each being defined as a line passing through each center point of each contiguous intra-cell compartment of an inflatable cell;
said compartmental bonds of said intra-cell compartments, during inflation, being drawn towards each other to decrease a distance therebetween and towards the center point of said intra-cell compartments to decrease a distance therebetween, so as to provide for circumferential constriction.

16. The device of claim 15 wherein a ratio of said second center point circumference to said first center point circumference is about 0.64.

17. An automatic portable ambulant system for applying pressure to a body limb, comprising:
a sleeve including first and second inflatable cells;
said first and second inflatable cells each including at least three intra-cell compartments;
said intra-cell compartments being confluent;
said intra-cell compartments being elongated along a primary axis of a body limb;
said first and second inflatable cells being adjacent to each other so as to be adapted to be arranged coaxially with respect to the primary axis of a body limb;
said first and second inflatable cells each including inner and outer shells of durable flexible material;
said inner and outer shells being bonded together to form a perimetric bond about a perimeter of the inflatable cell, said perimetric bond defining the inflatable cell as a volume between said inner and outer shells and within the perimetric bond;
said inner and outer shells being further bonded together to form a plurality of compartmental bonds within the inflatable cell bond, said plurality of compartmental bonds defining at least three intra-cell compartments
said perimetric cell bond including first and second perimetric cell bond portions, said first and second perimetric cell bond portions being substantially parallel thereto, wherein a portion of said compartmental bonds partly extending between said first and second perimetric cell bond portions;
said compartmental bonds extending between said first and second perimetric cell bond portions including perforations to allow for confluent airflow between adjacent intra-cell compartments within a cell;
said first inflatable cell becoming circumferentially constricted when said intra-cell compartments of said first inflatable cell are inflated;
said second inflatable cell becoming circumferentially constricted when said intra-cell compartments of said second inflatable cell are inflated;
said first and second inflatable cells being non-confluent such that the first and second inflatable cells are separately inflatable;
means for laterally coupling the outermost intra-cell compartments within a cell so as to form said sleeve into a substantially cylindrical shape; and
a portable hand-held pump unit for intermittently inflating any one or more selected cells of the sleeve via a conduit, said pump unit including a control unit for determining a treatment specificity of each cell and for determining a timing sequence for inflating of each cell based on the determined treatment specificity of each cell;
said sleeve having a first intra-cell compartment center point circumference when said intra-cell compartments are deflated and a second intra-cell compartment center point circumference when said intra-cell compartments are inflated, said second intra-cell compartment center point circumference being less than said first intra-cell compartment center point circumference so as to provide for circumferential constriction, said first and second intra-cell compartment center point circumferences, each being defined as a line passing through each center point of each contiguous intra-cell compartment of an inflatable cell;
said compartmental bonds of said intra-cell compartments, during inflation, being drawn towards each other to decrease a distance therebetween and towards the center point of said intra-cell compartments to decrease a distance therebetween, so as to provide for circumferential constriction.

18. The system of claim 17 wherein said pump unit is battery operated.

19. The system of claim 18 wherein said pump unit comprises a rechargeable battery.

20. The system of claim 17 wherein said pump unit comprises an air compressor.

21. The system of claim 17 wherein said conduit comprises a single tube for delivering fluid to said sleeve.

22. The system of claim 21 wherein said conduit comprises means for indicating to said control unit the treatment specificity of each cell.

23. The system of claim 17 wherein a ratio of said second center point circumference to said first center point circumference is about 0.64.

24. The system of claim 17 wherein said sleeve comprises at least one self-operated valve.

25. A device for applying pressure to a body limb having a primary axis, comprising:
    first and second inflatable cells;
    said first and second inflatable cells each including at least three intra-cell compartments;
    said intra-cell compartments being confluent;
    said intra-cell compartments being elongated along a primary axis of the limb and being substantially rectangular in shape when deflated and substantially cylindrical in shape when inflated;
    said first and second inflatable cells being adjacent each other and arranged coaxially with respect to the primary axis of the limb;
    said first and second inflatable cells each including inner and outer shells of durable flexible material;
    said first and second inflatable cells each including inner and outer shells of durable flexible material;
    said inner and outer shells being bonded together to form a perimetric bond about a perimeter of the inflatable cell, said perimetric bond defining the inflatable cell as a volume between said inner and outer shells and within the perimetric bond;
    said inner and outer shells being further bonded together to form a plurality of compartmental bonds within the inflatable cell bond, said plurality of compartmental bonds defining at least three intra-cell compartments
    said perimetric cell bond including first and second perimetric cell bond portions, said first and second perimetric cell bond portions being substantially parallel thereto, wherein a portion of said compartmental bonds partly extending between said first and second perimetric cell bond portions;
    said compartmental bonds extending between said first and second perimetric cell bond portions including perforations to allow for confluent airflow between adjacent intra-cell compartments within a cell;
    said first inflatable cell becoming circumferentially constricted when said intra-cell compartments of said first inflatable cell are inflated;
    said second inflatable cell becoming circumferentially constricted when said intra-cell compartments of said second inflatable cell are inflated;
    said first and second inflatable cells being non-confluent such that said first and second inflatable cells are separately inflatable;
    means for laterally coupling the outermost intra-cell compartments within a cell so as to form a sleeve into a substantially cylindrical shape;
    inflating means for intermittently inflating the first and second inflatable cells; and
    control means for determining a treatment specificity of each cell and for determining a timing sequence for inflating of each cell based on the determined treatment specificity of each cell;
    said sleeve having a first intra-cell compartment center point circumference when said intra-cell compartments are deflated and a second intra-cell compartment center point circumference when said intra-cell compartments are inflated, said second intra-cell compartment center point circumference being less than said first intra-cell compartment center point circumference so as to provide for circumferential constriction, said first and second intra-cell compartment center point circumferences, each being defined as a line passing through each center point of each contiguous intra-cell compartment of an inflatable cell;
    said compartmental bonds of said intra-cell compartments, during inflation, being drawn towards each other to decrease a distance therebetween and towards the center point of said intra-cell compartments to decrease a distance therebetween, so as to provide for circumferential constriction.

26. The device of claim 25 wherein a ratio of said second center point circumference to said first center point circumference is about 0.64.

27. An automatic portable ambulant system for applying pressure to a body limb, comprising:
    a sleeve including first and second inflatable cells;
    said first and second inflatable cells each including at least three intra-cell compartments;
    said intra-cell compartments being confluent;
    said intra-cell compartments being elongated along a primary axis of a limb and being substantially rectangular in shape when deflated and substantially cylindrical in shape when inflated;
    said first and second inflatable cells being adjacent each other and arranged coaxially with respect to the primary axis of the limb;
    said first and second inflatable cells each including inner and outer shells of durable flexible material;
    said inner and outer shells being bonded together to form a perimetric bond about a perimeter of the inflatable cell, said perimetric bond defining the inflatable cell as a volume between said inner and outer shells and within the perimetric bond;
    said inner and outer shells being further bonded together to form a plurality of compartmental bonds within the inflatable cell bond, said plurality of compartmental bonds defining at least three intra-cell compartments
    said perimetric cell bond including first and second perimetric cell bond portions, said first and second perimetric cell bond portions being substantially parallel thereto, wherein a portion of said compartmental bonds partly extending between said first and second perimetric cell bond portions;
    said compartmental bonds extending between said first and second perimetric cell bond portions including perforations to allow for confluent airflow between adjacent intra-cell compartments within a cell;
    said first inflatable cell becoming circumferentially constricted when said intra-cell compartments of said first inflatable cell are inflated;
    said second inflatable cell becoming circumferentially constricted when said intra-cell compartments of said second inflatable cell are inflated;

said first and second inflatable cells being non-confluent such that said first and second inflatable cells are separately inflatable;

means for laterally coupling the outermost intra-cell compartments within a cell so as to form said sleeve into a substantially cylindrical shape; and a portable hand-held pump unit for intermittently inflating any one or more selected cells of the sleeve via a conduit, said pump unit including a control unit for determining a treatment specificity of each cell and for determining a timing sequence for inflating of each cell based on the determined treatment specificity of each cell;

said sleeve having a first intra-cell compartment center point circumference when said intra-cell compartments are deflated and a second intra-cell compartment center point circumference when said intra-cell compartments are inflated, said second intra-cell compartment center point circumference being less than said first intra-cell compartment center point circumference so as to provide for circumferential constriction, said first and second intra-cell compartment center point circumferences, each being defined as a line passing through each center point of each contiguous intra-cell compartment of an inflatable cell;

said compartmental bonds of said intra-cell compartments, during inflation, being drawn towards each other to decrease a distance therebetween and towards the center point of said intra-cell compartments to decrease a distance therebetween, so as to provide for circumferential constriction.

28. The system of claim 27 wherein a ratio of said second center point circumference to said first center point circumference is about 0.64.

29. The system of claim 27 wherein said conduit comprises a single tube for delivering fluid to said sleeve.

30. The system of claim 29 wherein said conduit comprises means for indicating to said control unit the treatment specificity of each cell.

31. The system of claim 27 wherein said sleeve comprises at least one self-operated valve.

32. An automatic portable ambulant system for applying pressure to a body limb having a primary axis, comprising:
an inflatable cell; and
said inflatable cell including at least two intra-cell compartments;
said intra-cell compartments being confluent, each compartment being elongated in a direction of the primary axis; and
said inflatable cell further including inner and outer shells of durable flexible material;
said inner and outer shells being bonded together to form a perimetric cell bond;
said inner and outer shells being further bonded together to form compartmental bonds within said perimetric cell bond, said perimetric bond and said compartmental bonds defining the intra-cell compartment;
said perimetric cell bond including upper and lower perimetric cell bonds;
said compartmental bonds partly extending between said upper and lower perimetric cell bonds;
said compartmental bonds including perforations to allow for confluent airflow between adjacent intra-cell compartments within said cell, adjacent intra-cell compartments being spatially fixed relative to each other, such that upon inflation, said cell becomes circumferentially constricted;

said inflatable cell having a first center point circumference when said intra-cell compartments are deflated and a second center point circumference when said intra-cell compartments are inflated, said second center point circumference being less than said first center point circumference so as to provide for circumferential constriction, said first and second center point circumferences, each being defined as a line passing through each center point of each contiguous intra-cell compartment of an inflatable cell;

said compartmental bonds, during inflation, being drawn towards each other to decrease a distance therebetween and towards the center point of said intra-cell compartments to decrease a distance therebetween, so as to provide for circumferential constriction;

a portable hand-held pump unit for intermittently inflating said inflatable cell via a conduit;

said portable hand-held pump unit including a control unit for determining a treatment specificity of said inflatable cell and for determining a timing sequence for inflating of said inflatable cell based on the determined treatment specificity of said inflatable cell.

33. The system of claim 32 wherein said portable hand-held pump unit is battery operated.

34. The system of claim 32 wherein said portable hand-held pump unit comprises a rechargeable battery.

35. The system of claim 32 wherein said portable hand-held pump unit comprises an air compressor.

36. The system of claim 32 wherein said conduit comprises single tube for delivering fluid to said inflatable cell.

37. The system of claim 32 wherein said conduit comprises means for indicating to said control unit the treatment specificity of said inflatable cell.

38. The system of claim 32 wherein said inflatable cell comprises at least one self operated valve.

39. An automatic portable ambulant system for applying pressure to a body limb having a primary axis, comprising:
an inflatable cell, said inflatable cell including at least two intra-cell compartments; said intra-cell compartments being confluent, each compartment being elongated in a direction of the primary axis; and
said inflatable cell further including inner and outer shells of durable flexible material;
said inner and outer shells being bonded together to form a perimetric cell bond;
said inner and outer shells being further bonded together to form compartmental bonds within said perimetric cell bond, said perimetric bond and said compartmental bonds defining the intra-cell compartment;
said perimetric cell bond including upper and lower perimetric cell bonds;
said compartmental bonds partly extending between said upper and lower perimetric cell bonds;
said compartmental bonds including perforations to allow for confluent airflow between adjacent intra-cell compartments within said cell, adjacent intra-cell compartments being spatially fixed relative to each other, such that upon inflation of said cell, said cell becomes circumferentially constricted;
said inflatable cell having a center point circumference of $N\pi r$ when said cell is deflated and a center point circumference of $2Nr$ when said cell is inflated, where N is the number of intra-cell compartments in said cell, and where r is the cross-sectional radius of each compartment when inflated, the center point circumference being a line passing through each center point of each adjacent intra-cell compartment of said inflatable cell;

said compartmental bonds, during inflation, being drawn towards each other to decrease a distance therebetween and towards the center point of said intra-cell compartments to decrease a distance therebetween, so as to provide for circumferential constriction;

a portable hand-held pump unit for intermittently inflating said inflatable cell via a conduit;

said portable hand-held pump unit including a control unit for determining a treatment specificity of said inflatable cell and for determining a timing sequence for inflating of said inflatable cell based on the determined treatment specificity of said inflatable cell.

40. The system of claim 39, wherein said portable hand-held pump unit is battery operated.

41. The system of claim 40, wherein said portable hand-held pump unit comprises a rechargeable battery.

42. The system of claim 40, wherein said portable band-held pump unit comprises an air compressor.

43. The system of claim 40, wherein said conduit comprises a single tube for delivering fluid to said sleeve.

44. The system of claim 40, wherein said conduit comprises means for indicating to said control unit the treatment specificity of said inflatable cell.

45. The system of claim 40, wherein said sleeve comprises at least one self-operated valve.

* * * * *